US00PP29064P3

(12) United States Plant Patent
Van Swieten

(10) Patent No.: US PP29,064 P3
(45) Date of Patent: Mar. 6, 2018

(54) ***PHALAENOPSIS* ORCHID PLANT NAMED 'PHALFPYJA'**

(50) Latin Name: ***Phalaenopsis* hybrid**
Varietal Denomination: PHALFPYJA

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 30 days.

(21) Appl. No.: 14/999,657

(22) Filed: Jun. 9, 2016

(65) Prior Publication Data

US 2017/0359934 P1 Dec. 14, 2017

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

(56) References Cited

PUBLICATIONS

UPOV-PLUTO: Plant Variety Database, updated on Aug. 9, 2017, citation for 'PHALFPYJA' (1 page).*
EU Community Plant Variety Office Official Gazette, 3.2014, Jun. 15, 2014, cover page and pp. 37, 56.
EU Community Plant Variety Office Official Gazette, 1.2015, Feb. 15, 2015, cover page and p. 75.
EU Community Plant Variety Rights Application No. 2015/2217, Application n°A201501732, filed Sep. 24, 2015, 8 pages.
EU Community Plant Variety Office Official Gazette, 6.2015, Dec. 15, 2015, cover page and pp. 36, 55.

* cited by examiner

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHALFPYJA', particularly characterized by having white flecked and dotted flowers with mottled leaves, the intensity and size of the flecks and dots is temperature dependent, the flecks and dots are larger at the base and become smaller towards the edge, 1 to 3 peduncles that are medium-long and moderate, leaves that are lanceolate, and is propagated by meristem tissue culture, is disclosed.

3 Drawing Sheets

Genus and species: *Phalaenopsis* hybrid.
Variety denomination: 'PHALFPYJA'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFPYJA'.

The new *Phalaenopsis* plant is a product of a planned breeding program conducted by the inventor in Bleiswijk, The Netherlands. The objective of this breeding program was to create a new *Phalaenopsis* plant with numerous attractive and unique white flecked and dotted flowers with mottled leaves, suitable for potted plant production.

The new *Phalaenopsis* plant 'PHALFPYJA' is a result of cross-pollination made by the inventor in April 2007 in Bleiswijk, The Netherlands of the proprietary white flecked female, or seed parent, *Phalaenopsis* hybrid '01-1920' (unpatented) with the proprietary male, or pollen parent, *Phalaenopsis* hybrid '01-1523' (unpatented).

The new *Phalaenopsis* was selected by the inventor as a single plant within the progeny of the stated cross-pollination in a controlled greenhouse in Bleiswijk, The Netherlands in April 2010. Asexual reproduction of the new *Phalaenopsis* plant by meristem tissue culture since 2013 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Sep. 24, 2015. 'PHALFPYJA' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALFPYJA' as a new and distinct variety of *Phalaenopsis* plant.

1) White-flecked and dotted flowers with mottled leaves, the intensity and size of the flecks and dots is temperature dependent, and the flecks and dots are larger at the base and become smaller towards the edge;
2) 1 to 3 peduncles;
3) Peduncle is medium-long and moderate; and
4) Shape of the leaf is lanceolate.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 50-week old plants in January 2016. Colors in the photographs may differ from the color values cited in the detailed botanical description, which accurately describe the actual colors of the new variety.

DESCRIPTION OF THE NEW VARIETY

Figure 1:
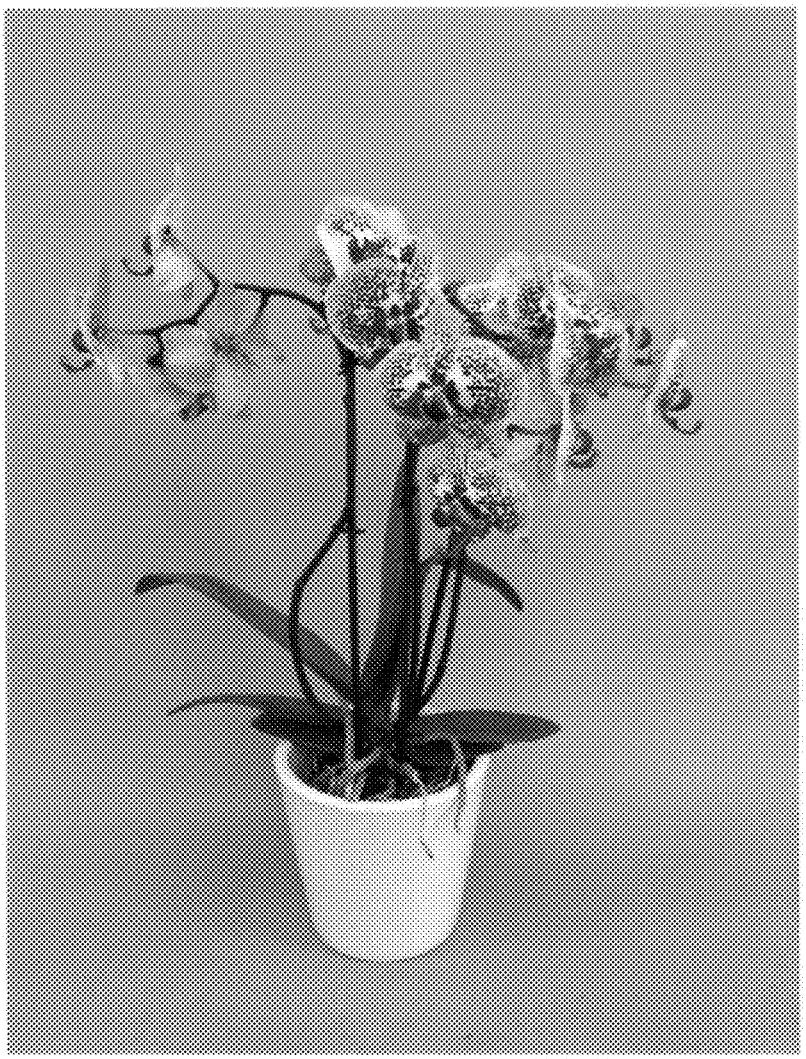
FIG. 1 shows the overall plant habit, including blooms and foliage of 'PHALFPYJA'.
Figure 2:
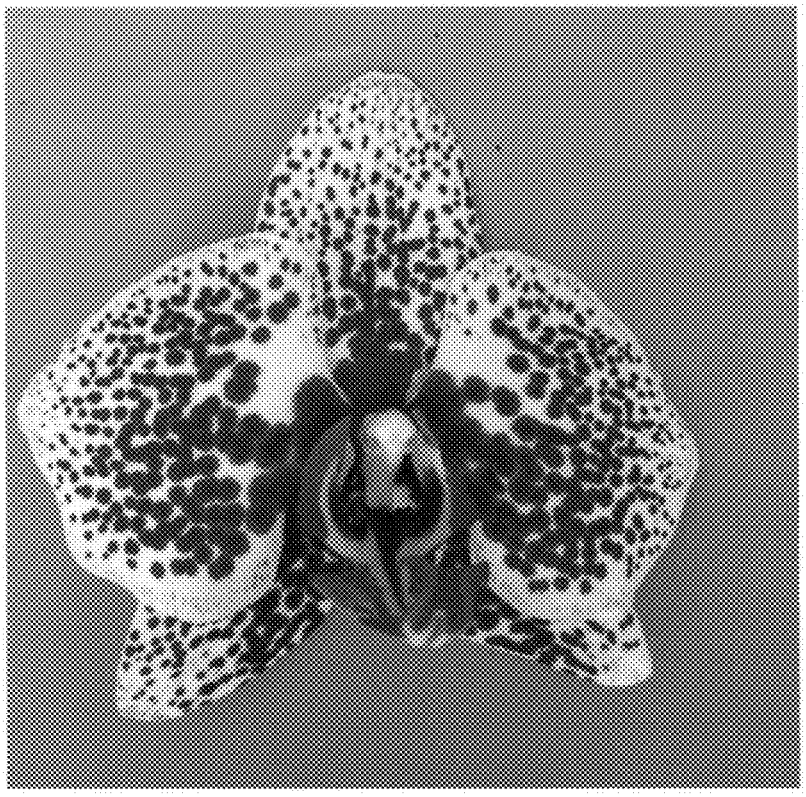
FIG. 2 shows a close-up of a flower of 'PHALFPYJA'.
Figure 3:
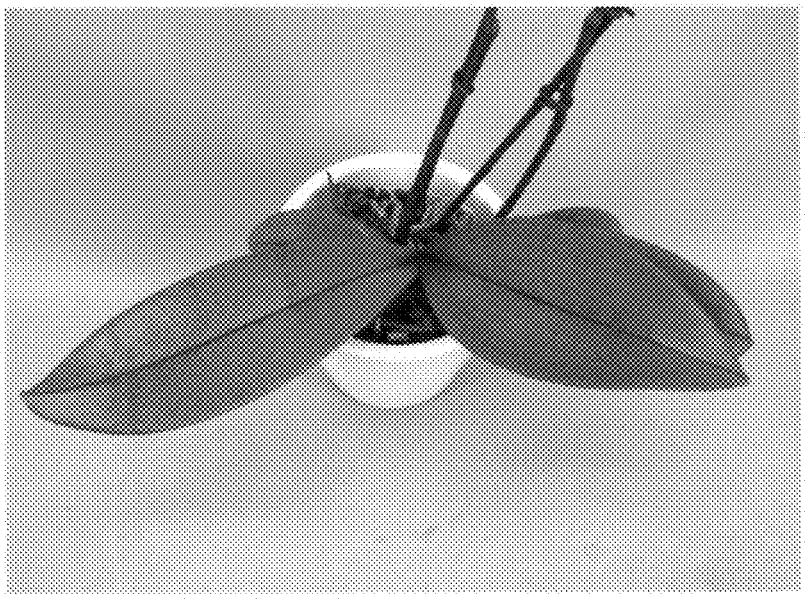
FIG. 3 shows a close-up of the leaves of 'PHALFPYJA'.

The following detailed description sets forth the distinctive characteristics of 'PHALFPYJA'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in January 2016 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—*Phalaenopsis*.

*Variety name*.—'PHALFPYJA'.

Parentage:

*Female parent*.—*Phalaenopsis* cultivar '01-1920' (unpatented).

*Male parent*.—*Phalaenopsis* cultivar '01-1523' (unpatented).

Propagation:

*Type*.—Meristem tissue culture.

Roots:

*Root description*.—Greyed-green colored roots with lateral roots having light purple colored root tips.

Plant:

*Commercial crop time to flowering*.—Approximately 48 to 50 weeks from a rooted cutting to finish in a 12 cm pot.

*Growth habit of peduncle*.—Standard, green/greyed-green mottled leaves, raceme to panicle.

*Height (from soil level to top of inflorescence)*.—Approximately 34.0 cm to 44.0 cm.

*Width (measured from leaf tips)*.—About 29.0 cm to 33.0 cm.

*Vigor*.—Strong.

Leaves:

*Mature leaves*.—Quantity per plant: 6 to 8 leaves are produced before flowering. Length (fully expanded): 18.0 cm to 21.0 cm. Width: 6.5 cm to 7.5 cm. Shape: Lanceolate. Base shape: Moderately elongated. Apex: Unequal obtuse. Leaf blade angle with the petiole (measured from the horizontal position): Between 25 degrees and 50 degrees. Leaf margin: Entire. Color: Upper surface: RHS 147B, mottled RHS 146B. Lower surface: RHS 146A. Texture: Smooth. Thickness: 1.6 mm to 1.9 mm. Venation: Pattern: Parallel. Color of the midvein: Upper surface: RHS 146A. Lower surface: RHS 187A.

Peduncle:

*Quantity per plant*.—1 to 3.

*Number of flowers per peduncle*.—8 to 12.

*Length*.—30.0 cm to 35.0 cm.

*Diameter*.—3.5 mm to 3.9 mm.

*Strength*.—Moderate.

*Aspect*.—Upright to slightly pendant.

*Texture*.—Slightly rough.

*Color*.—Mix of green (RHS 144A) and greyed-purple (RHS 187A).

*Internode length*.—3.5 cm to 4.5 cm.

*Callosities*.—None.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 100.0 mm to 120.0 mm.

*Flowering time*.—First flowers can be expected 10 to 11 months after planting in a 12 cm (diameter) pot.

*Flower*.—Height: 77.0 mm to 82.0 mm. Diameter: 78.0 mm to 83.0 mm. Depth of lip: 19.0 mm to 21.0 mm.

*Flower longevity*.—On the plant: 8 to 12 weeks.

*Fragrance*.—Absent.

*Flower bud*.—Average size: Medium to large. Length: 21.0 mm to 23.0 mm. Width: 16.0 mm to 18.0 mm. Shape: Egg shaped. Color: Green (RHS N144D) with a touch of greyed-red (RHS 182B) and diluted dots (RHS 187A).

*Petals*.—Arrangement: Open/free. Shape: Semi-circular. Apex: Rounded asymmetric. Margin: Slightly undulated. Length (from base to tip): 38.0 mm to 40.0 mm. Width: 43.0 mm to 45.0 mm. Color (when fully opened): Upper surface: Basic color: White (RHS NN155C), flecked and dotted (RHS N79C and 187B). Over color: Light purple at the apex (RHS N75A). Lower surface: Basic color: White (RHS NN155C) with diluted flecks and dots (RHS N79A). Over color: Light purple apex (RHS N75A).

*Dorsal sepal*.—Shape: Elliptic. Apex: Emarginated symmetric. Margin: Entire. Length (from base to tip): 40.0 mm to 42.0 mm. Width: 27.0 mm to 29.0 mm. Color (when fully opened): Upper surface: Basic color: White (RHS NN155C), flecked and dotted (RHS N79C and 187A). Over color: Light purple apex (RHS 75B). Lower surface: Basic color: White (RHS NN155C) with diluted dots (RHS N79B). Over color: Light purple (RHS 75B).

*Lateral sepals*.—Shape: Ovate. Apex: Obtuse symmetric. Margin: Entire. Length (from base to tip): 43.0 mm to 45.0 mm. Width: 27.0 mm to 29.0 mm. Color (when fully opened): Upper surface: Basic color: White (RHS NN155C), flecked and dotted (RHS 187B and N79B). Over color: Slightly light green on one side (RHS 145C) and light purple at the apex (RHS 75B). Lower surface: Basic color: White (RHS NN155C) with diluted flecks and dots (RHS 187A to 187B and N79B). Over color: Light green (RHS 145A to 145B) with light purple vein towards the apex (RHS 75A).

*Labellum* (*lip*).—Margin: Entire. Whiskers: Present. Length of whiskers: 15.0 mm to 17.0 mm. Color of whiskers: Dark purple (RHS N79B and 59A). Pubescence on the lip: Absent.

*Lateral lobe*.—Shape: Spatulate. Length (from base to tip): 18.0 mm to 20.0 mm. Width: 13.0 mm to 15.0 mm. Color: Purple (RHS N78A) and red-purple (RHS 59B), white in the middle (RHS NN155C) with a touch of yellow (RHS 12A).

*Apical lobe*.—Shape: Triangular/trullate. Length: 19.0 mm to 21.0 mm. Width: 20.0 mm to 22.0 mm. Color: Red-purple/purple (RHS 60A and N78A) with yellow at the base and in the middle (RHS 8B).

*Callus*.—Average size: Medium. Height: 0.5 mm to 0.7 mm. Length: 0.5 mm to 0.7 mm. Width: 0.3 mm to 0.5 mm. Color: Dark purple (RHS N78A) and yellow on the sides (RHS 3C).

*Reproductive organs*.—Column: Length: 9.0 mm to 11.0 mm. Diameter: 5.2 mm to 5.4 mm. Color: White at the base (RHS NN155C) and purple towards the tip (RHS N78B). Pollinia: Quantity: 2. Diameter: 1.2 mm to 1.4 mm. Color: Orange (RHS N25B). Ovary (part of pedicel with small ribs towards the column): Length: 10.0 mm to 12.0 mm. Diameter: 2.4 mm to 2.6 mm. Pedicel: Length: 39.0 mm to 41.0 mm. Diameter: 2.7 mm to 3.0 mm. Color: Brown at the base (RHS 200A), light green (RHS 146B/C) and greyed-red (RHS 182A to 182B) towards the flower.

Disease, pest, and stress resistance: No specific resistance or susceptibility observed to pathogens and pests common to *Phalaenopsis*.

Fruit and seeds: Fruit and seed development has not been observed on plants of the new *Phalaenopsis* to date.

COMPARISON WITH PARENTAL AND COMMERCIAL VARIETIES

'PHALFPYJA' differs from female parent plant '01-1920' (unpatented) in that 'PHALFPYJA' has flowers with flecks and dots that are spread out over the entire surface and whiskers that are dark purple, whereas '01-1920' has flowers with flecks and dots that are more intense at the center of the flower and whiskers that are white. Additionally, 'PHALFPYJA' has a red-purple apical lobe with a yellow base, whereas '01-1920' has a yellow-white apical lobe.

The male parent of 'PHALFPYJA', cultivar '01-1523' (unpatented), is no longer in existence, so a meaningful comparison cannot be made.

'PHALFPYJA' is most similar to the commercial *Phalaenopsis* plants named 'PHALFOYX' (U.S. Plant patent application Ser. No. 14/757,344) and 'PHALACPY' (unpatented). 'PHALFPYJA' differs from the commercial variety 'PHALFOYX' in that 'PHALFPYJA' has mottled leaves and flowers that are not edged, whereas 'PHALFOYX' has leaves that are not mottled and flowers that are edged. Additionally, 'PHALFPYJA' has an apical lobe that is evenly colored and is darker purple than 'PHALFOYX', whereas 'PHALFOYX' has an apical lobe that is spotted and is lighter purple than 'PHALFPYJA'.

'PHALFPYJA' differs from the commercial variety 'PHALACPY' in that 'PHALFPYJA' has an apical lobe of the lip that is red-purple/purple at the base and yellow in the middle and a lateral lobe of the lip that is purple and red-purple with white in the middle and a touch of yellow, whereas 'PHALACPY' has an apical lobe of the lip that is white with yellow and greyed-red at the base and a lateral lobe of the lip that is white with two stripes at the base and yellow on one side. Additionally, 'PHALFPYJA' has flowers with no edge and whiskers that are dark purple, whereas 'PHALACPY' has flowers with a light purple edge and whiskers that are white.

I claim:

1. A new and distinct variety of *Phalaenopsis* plant named 'PHALFPYJA', substantially as described and illustrated herein.

* * * * *